United States Patent
Liu (10) Patent No.: US 11,291,363 B2
(45) Date of Patent: Apr. 5, 2022

(54) INSPECTION INSTRUMENT WITH AUTOMATIC STRABISMUS DETECTION MECHANISM, AND INSPECTION METHOD THEREOF

(71) Applicant: Dongguang Liu, Guangzhou (CN)

(72) Inventor: Dongguang Liu, Guangzhou (CN)

(*) Notice: Subject to any disclaimer, the term of this patent is extended or adjusted under 35 U.S.C. 154(b) by 0 days.

(21) Appl. No.: 16/630,516

(22) PCT Filed: Nov. 29, 2018

(86) PCT No.: PCT/CN2018/121574
§ 371 (c)(1),
(2) Date: Jan. 13, 2020

(87) PCT Pub. No.: WO2020/107545
PCT Pub. Date: Jun. 4, 2020

(65) Prior Publication Data
US 2021/0282637 A1 Sep. 16, 2021

(30) Foreign Application Priority Data

Nov. 29, 2018 (CN) .......................... 201811447610.0
Nov. 29, 2018 (CN) .......................... 201821996265.1

(51) Int. Cl.
*A61B 3/08* (2006.01)
*G02B 5/04* (2006.01)

(52) U.S. Cl.
CPC ................ *A61B 3/085* (2013.01); *G02B 5/04* (2013.01)

(58) Field of Classification Search
CPC ........... A61B 3/085; A61B 3/08; A61B 3/113; A61B 3/02; A61B 3/14; A61B 3/0025;
(Continued)

(56) References Cited

U.S. PATENT DOCUMENTS 5,094,521 A * 3/1992 Jolson .................... A61B 3/085
351/206
5,262,806 A * 11/1993 Szirth .................... A61B 3/085
351/210
(Continued)

FOREIGN PATENT DOCUMENTS

JP 87102898 A * 4/1988 ............... A61B 3/08
JP 107898430 A * 4/2018 ............... A61B 3/08

OTHER PUBLICATIONS

Feng Z; CN 87102898 A; dated Apr. 1988; Japan; English Machine Translation.*
(Continued)

*Primary Examiner* — William R Alexander
*Assistant Examiner* — Sharrief I Broome
(74) *Attorney, Agent, or Firm* — Rumit Ranjit Kanakia (57) ABSTRACT

An automatic strabismus detection mechanism includes a housing and an eyepiece arranged on the housing. A lens mechanism located on a same axis as the eyepiece is arranged in the housing. The lens mechanism is provided with a rotating mechanism for adjusting an angle of refraction. The automatic strabismus detection mechanism includes technical effects of being composed of the lens mechanism and automatically controlled to generate 0 to 50 prism degrees; the volume is small and the weight is light, which is lighter than that of a triangular prism block made of ordinary glass; and the manufacturing cost is low, which is about one fifth of the price of a lens row. Therefore, with the automatic strabismus detection mechanism, a variety of equipment and instruments based on the principle of triangular prism spectroscopic detection or dispersion is greatly improved, and development of related instruments and equipment is facilitated.

10 Claims, 6 Drawing Sheets

(58) Field of Classification Search
CPC ....... A61B 3/032; A61B 3/145; A61B 3/0091;
A61B 3/103; A61B 3/0285; A61B 3/10;
A61B 3/0008; A61B 3/0083; A61B
3/028; A61B 3/09; A61B 2560/0425;
A61B 3/00; A61B 3/024; A61B 3/04;
G02B 5/04
See application file for complete search history.

(56) References Cited

U.S. PATENT DOCUMENTS

| | | | | |
|---|---|---|---|---|
| 5,448,349 | A * | 9/1995 | Kosaka | G01N 15/1459 250/461.2 |
| 6,155,995 | A * | 12/2000 | Lin | A61F 7/02 601/148 |
| 6,523,954 | B1 * | 2/2003 | Kennedy | A61B 5/0013 351/205 |
| 2002/0085844 | A1 * | 7/2002 | Tashiro | G08B 13/19632 396/427 |
| 2016/0262936 | A1 * | 9/2016 | Belliappa | A61F 9/04 |

OTHER PUBLICATIONS

Liu D; CN 107898430 A; dated Apr. 2018; Japan; English Machine Translation.*

* cited by examiner

PIG.1

PIG.2

PIG.3

PIG.4

PIG.5

PIG.6

INSPECTION INSTRUMENT WITH AUTOMATIC STRABISMUS DETECTION MECHANISM, AND INSPECTION METHOD THEREOF

TECHNICAL FIELD

The disclosure relates to the technical field of eyesight inspection, and in particular to an automatic strabismus detection mechanism, an inspection instrument with the automatic strabismus detection mechanism, and an inspection method.

BACKGROUND

Strabismus refers to the inability of both eyes to focus on a target at the same time, which is a disease of extraocular muscles and may be divided into two categories: concomitant strabismus and paralytic strabismus. Conventional strabismus inspection methods include binocular visual function inspection, refractive inspection, eye position and angle-of-strabismus measurement, eye movement inspection, etc. Strabismus or not may be determined by the methods of eye appearance inspection, eyesight test and refractive inspection, covering test, eye movement inspection, and angle-of-strabismus inspection.

Further, a triangular prism is conventionally used for strabismus inspection. The triangular prism is a transparent body or optical instrument with a triangular cross section. The triangular prism is applied to strabismus inspection due to the characteristics of shifting a passing beam toward its tip and dispersing polychromatic light when passing.

At present, there are two types of triangular prisms on the market: one is a block-shaped triangular prism, where although the prism degree may be any number from 1 to 80, a triangular prism has only one invariable prism degree; the other one is a lens row-type triangular prism, which is formed by combining a plurality of prism blocks with different prism degrees in an ascending order of prism degrees and presents a stepped transparent lens row on an outer surface, where the prism degree of each prism block is also invariable.

When using a triangular prism perform dispersion, spectroscopic experiments, or strabismus inspection, it is often necessary to use a plurality of blocky triangular prisms or change triangular prism lens rows to obtain satisfactory results. There are disadvantages such as large number of triangular prisms or large overall volume, extremely inconvenient use, and high cost.

SUMMARY

In view of the shortcomings of the prior art, the disclosure aims to provide an automatic strabismus detection mechanism, an inspection instrument with the automatic strabismus detection mechanism, and an inspection method. Specifically, a lens mechanism and a rotating mechanism are arranged to achieve continuous adjustment of an angle of refraction, and a data acquisition device captures and outputs video data, so as to realize the intelligent strabismus inspection to the greatest extent.

In order to achieve the above objectives, the disclosure adopts the following technical solutions:

An automatic strabismus detection mechanism includes a housing and an eyepiece arranged on the housing. A lens mechanism located on a same axis as the eyepiece is arranged in the housing, where the lens mechanism is provided with a rotating mechanism for adjusting an angle of refraction.

It should be noted that the lens mechanism includes a first lens group, a second lens group, a movable connecting member, and filling liquid, the first lens group and the second lens group are arranged at two ends of the movable connecting member respectively, an internal closed space is formed by the first lens group, the second lens group and the movable connecting member, the rotating mechanism is connected with the second lens group, when the rotating mechanism rotates, the second lens group rotates synchronously, and the filling liquid is filled in the closed space.

It should be noted that the first lens group is composed of a first sealing cover and a first lens installed therein, the second lens group is composed of a second sealing cover and a second lens installed therein, the movable connecting member is connected with the first sealing cover and the second sealing cover respectively in a sealing manner, and the rotating mechanism is connected with the second sealing cover.

It should be noted that the rotating mechanism includes a motor, a worm, a worm gear, a rotating base, and a synchronous belt, two ends of the synchronous belt are arranged on a rotating shaft of the motor and one end of the worm respectively in a sleeving manner, the worm gear is connected with the worm in a meshing manner, the rotating base is arranged at the bottom of the worm gear, and the second lens group is connected with the rotating base.

As a preferred technical solution, the movable connecting member may be a silicone sleeve, and the filling liquid may be silicone oil.

As another embodiment of the disclosure:

A strabismus inspection instrument with an automatic strabismus detection mechanism includes an outer housing composed of a front outer housing and a rear outer housing, an inner housing arranged in the outer housing, and a window in positional correspondence with an eyepiece, further including:

a data acquisition device, configured to collect and analyze obtained eyesight test data and output the eyesight test data;

a covering device, arranged on one side of a lens mechanism, and configured to cover at least one eye to ensure that the other eye is inspected; and a control device, configured to control the cooperative work of the lens mechanism, the covering device and the data acquisition device.

It should be noted that the data acquisition device includes at least one camera and a plurality of guide lights, the camera and the plurality of guide lights are arranged in the inner housing respectively, the camera, the eyepiece and the lens mechanism are located on a same axis, and the plurality of guide lights is distributed outwards circumferentially with the camera as a circle center.

It should be noted that the covering device includes a rotating motor, a covering plate and a limiting sensor, a rotating shaft of the rotating motor is connected with the covering plate, the covering plate is provided with a limiting strip, and when the covering plate is in an uncovering or covering state, the limiting strip is located in the limiting sensor.

It should be noted that the control device includes a microprocessor and a display screen, the microprocessor is electrically connected with the lens mechanism, the covering device and the data acquisition device, respectively, and the display screen is configured to display the test data.

As an inspection method of an inspection instrument of the disclosure:

An inspection method of a strabismus inspection instrument includes the following steps:

S1: observing through a window with both eyes, and looking at a data acquisition device through a lens mechanism;

S2: covering, by a covering device, one eye that does not need to be inspected, and looking at the data acquisition device with the other eye that is being inspected;

S3: starting the lens mechanism and adjusting an angle of refraction as needed;

S4: collecting, by the data acquisition device, video data of the inspected eye; and S5: outputting the collected data.

It should be noted that the inspected eye looks at a flickering guide light of the data acquisition device during the inspection.

It should be further noted that the angle of refraction can be adjusted repeatedly and continuously.

The beneficial technical effects of the disclosure are as follows:

1. the automatic strabismus detection mechanism is composed of the lens mechanism and automatically controlled to generate 0 to 50 prism degrees;

2. the volume is small and the weight is light, which is lighter than that of a triangular prism block made of ordinary glass; and 3. the manufacturing cost is low, which is about one fifth of the price of a lens row.

Therefore, with the promotion and application of the automatic strabismus detection mechanism, a variety of equipment and instruments based on the principle of triangular prism spectroscopic detection or dispersion can be greatly improved, and the development of related instruments and equipment towards an intelligent direction is facilitated.

DETAILED DESCRIPTION

The disclosure will be further described below with reference to the accompanying drawings. It should be noted that on the premise of the technical solution, the following example gives detailed embodiments and specific operation processes, but the protection scope of the disclosure is not limited to this example.

Figure 1:
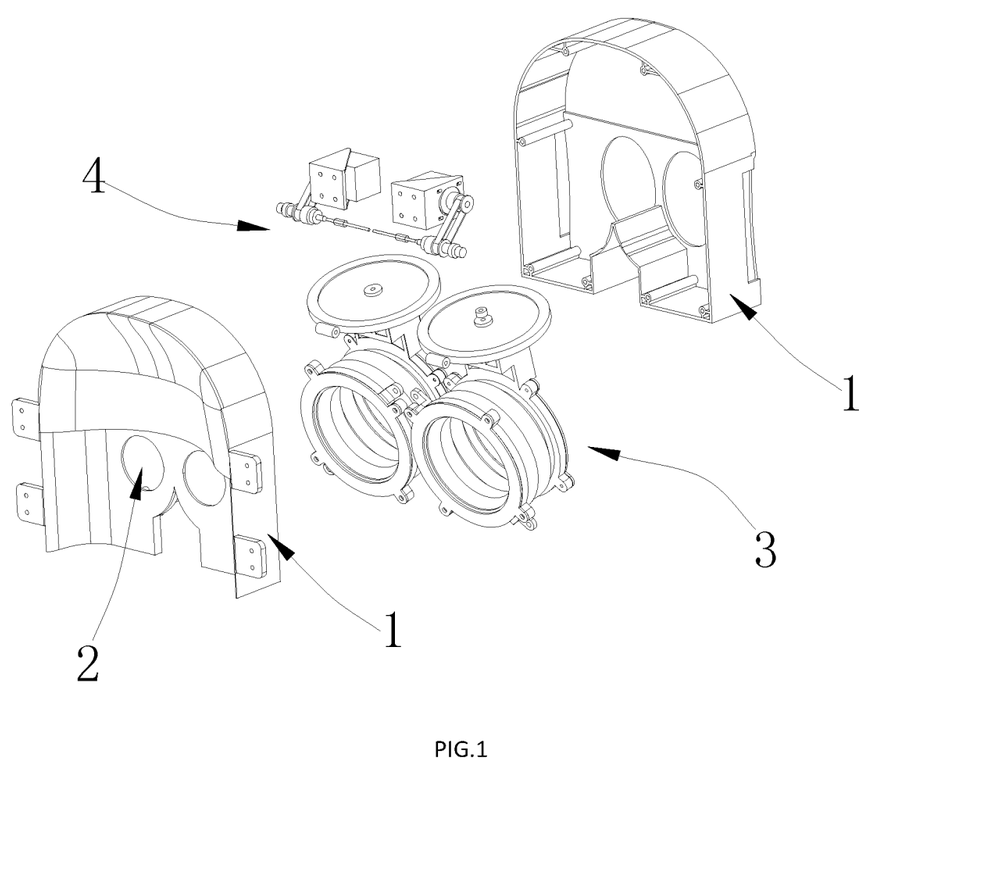
FIG. 1 is a schematic structure diagram of a lens mechanism and a rotating mechanism according to the disclosure.

As shown in FIG. 1, an automatic strabismus detection mechanism of the disclosure includes a housing 1 and an eyepiece 2 arranged on the housing 1. A lens mechanism 3 located on a same axis as the eyepiece 2 is arranged in the housing 1, where the lens mechanism 3 is provided with a rotating mechanism 4 for adjusting an angle of refraction.

Further, in order to meet the requirement of quick inspection, the lens mechanism, the rotating mechanism and the eyepiece may be provided in pairs.

Figure 2:
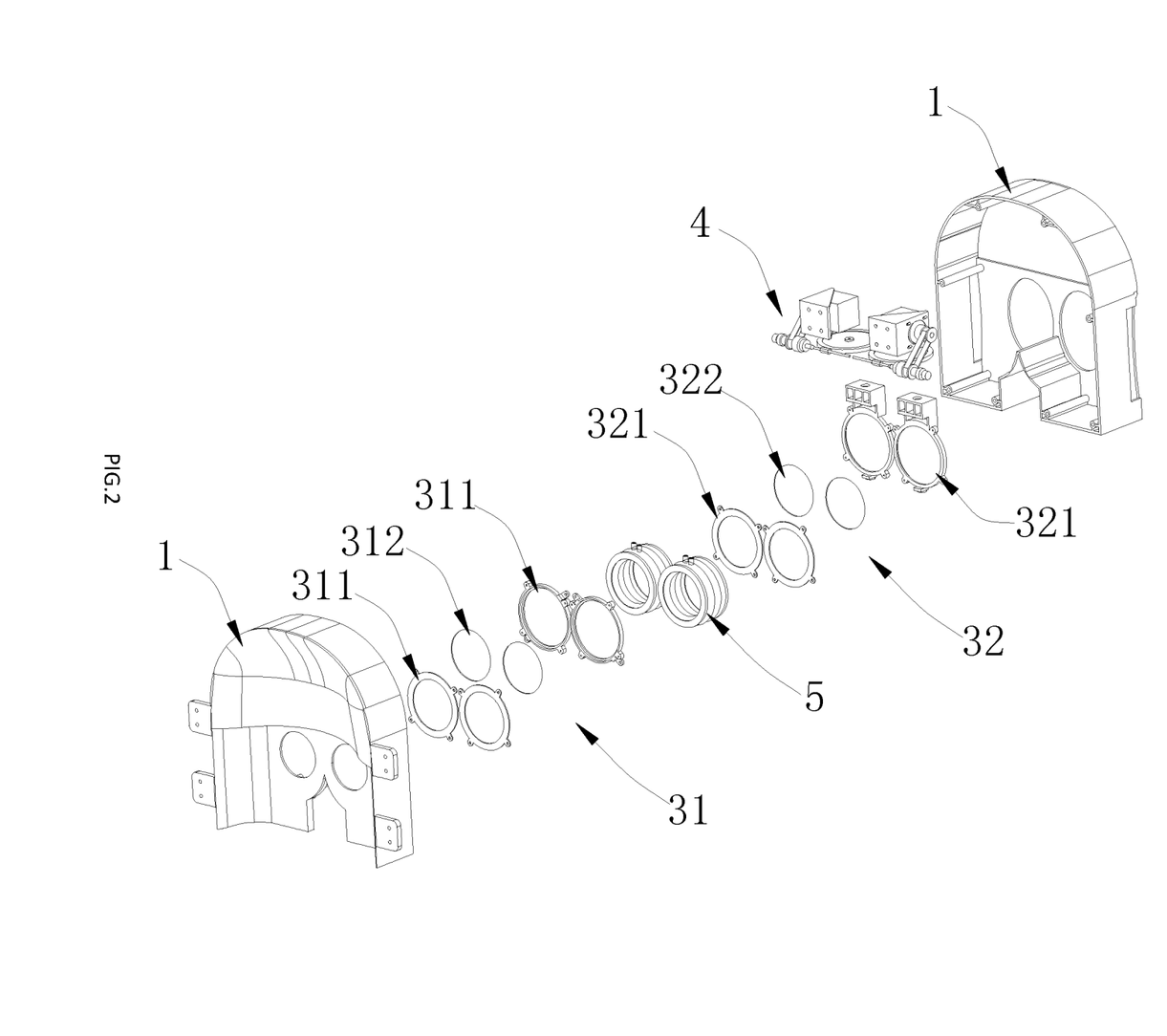
FIG. 2 is an exploded schematic structure diagram of FIG. 1.

Further, as shown in FIG. 2, the lens mechanism 3 includes a first lens group 31, a second lens group 32, a movable connecting member 5, and filling liquid, the first lens group 31 and the second lens group 32 are arranged at two ends of the movable connecting member 5 respectively, an internal closed space is formed by the first lens group 31, the second lens group 32 and the movable connecting member 5, the rotating mechanism 4 is connected with the second lens group 32, and the filling liquid is filled in the closed space.

Furthermore, as shown in FIG. 2, the first lens group 31 is composed of a first sealing cover 311 and a first lens 312 installed therein, the second lens group 32 is composed of a second sealing cover 321 and a second lens 322 installed therein, the movable connecting member 5 is connected with the first sealing cover 311 and the second sealing cover 321 respectively in a sealing manner, and the rotating mechanism 4 is connected with the second sealing cover 321.

As a preferred technical solution, the movable connecting member may be a silicone sleeve, and the filling liquid may be silicone oil.

In the aforementioned structure, when the rotating mechanism rotates, the second lens group rotates synchronously. Because a soft material of a silicone sleeve is arranged between the first lens group and the second lens group, when the second lens group rotates, the first lens group does not rotate.

Figure 3:
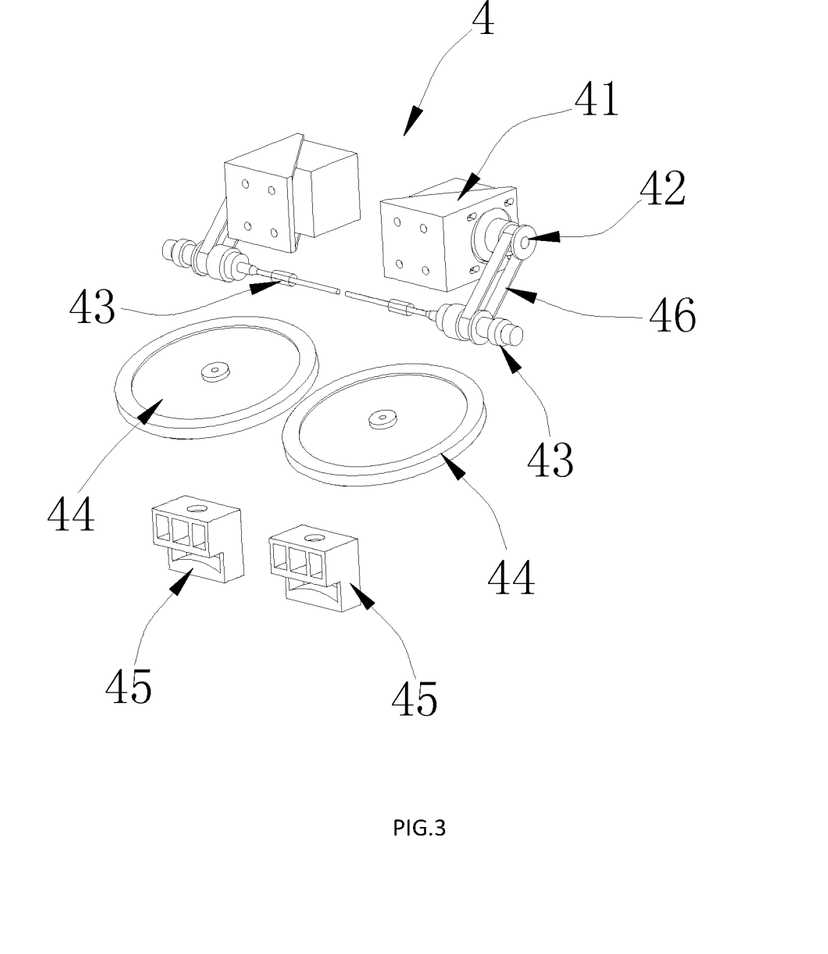
FIG. 3 is a schematic structure diagram of the rotating mechanism in FIG. 1 and FIG. 2.

As shown in FIG. 3, the rotating mechanism 4 includes a motor 41, a worm 43, a worm gear 44, a rotating base 45, and a synchronous belt 46, two ends of the synchronous belt 46 are arranged on a rotating shaft 42 of the motor 41 and one end of the worm 43 respectively in a sleeving manner, the worm gear 44 is connected with the worm 43 in a meshing manner, the rotating base 45 is arranged at the bottom of the worm gear 44, and the second lens group is connected with the rotating base 45.

Figure 4:
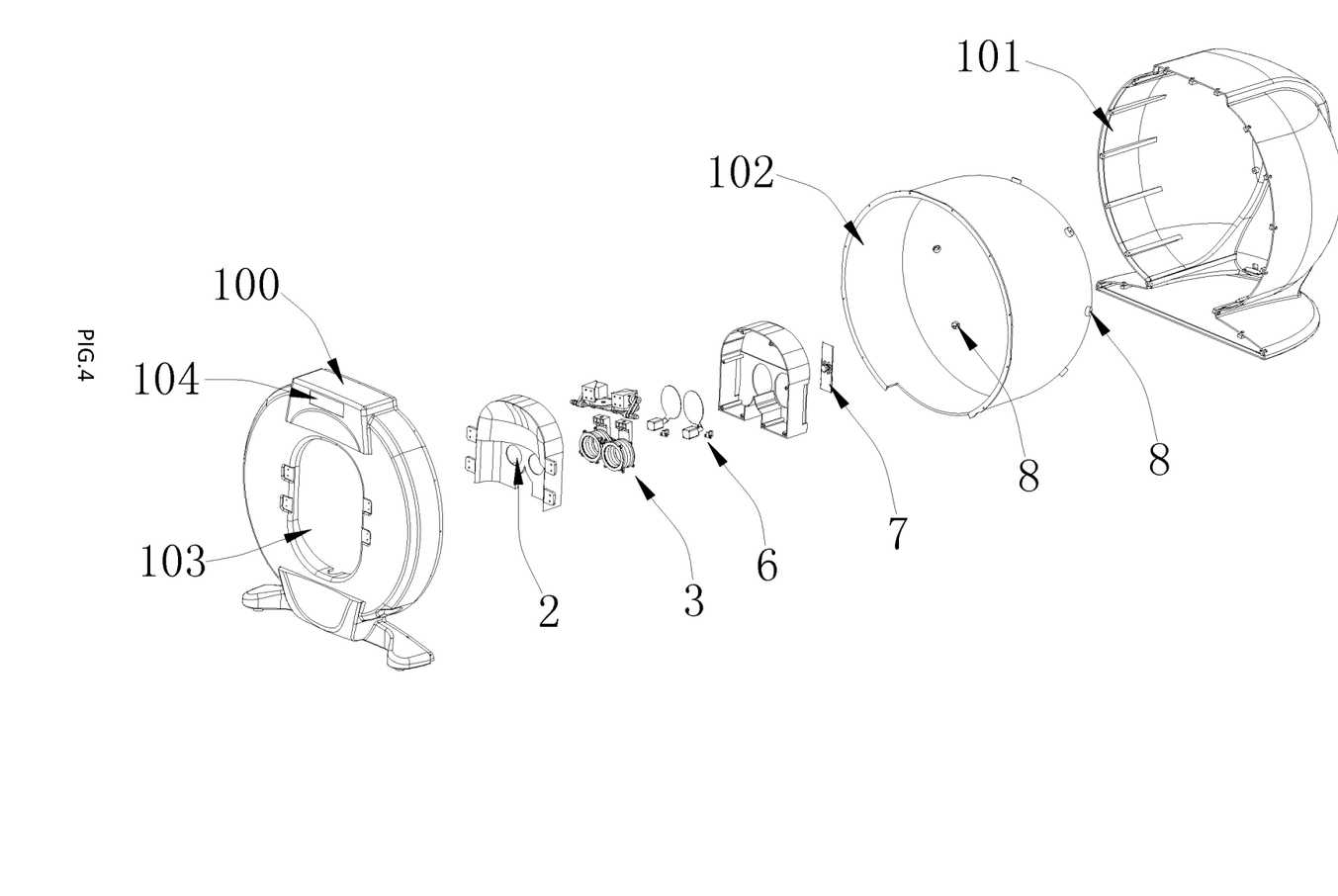
FIG. 4 is a schematic structure diagram of a strabismus inspection instrument according to the disclosure.

As another embodiment of the disclosure:

As shown in FIG. 4, a strabismus inspection instrument with an automatic strabismus detection mechanism includes an outer housing composed of a front outer housing 100 and a rear outer housing 101, an inner housing 102 arranged in the outer housing, and a window 103 in positional correspondence with an eyepiece 2, further including:

a data acquisition device, configured to collect and analyze obtained eyesight test data and output the eyesight test data;

a covering device 6, arranged on one side of a lens mechanism 3, and configured to cover at least one eye to ensure that the other eye is inspected; and a control device, configured to control the cooperative work of the lens mechanism 3, the covering device 6 and the data acquisition device.

Figure 5:
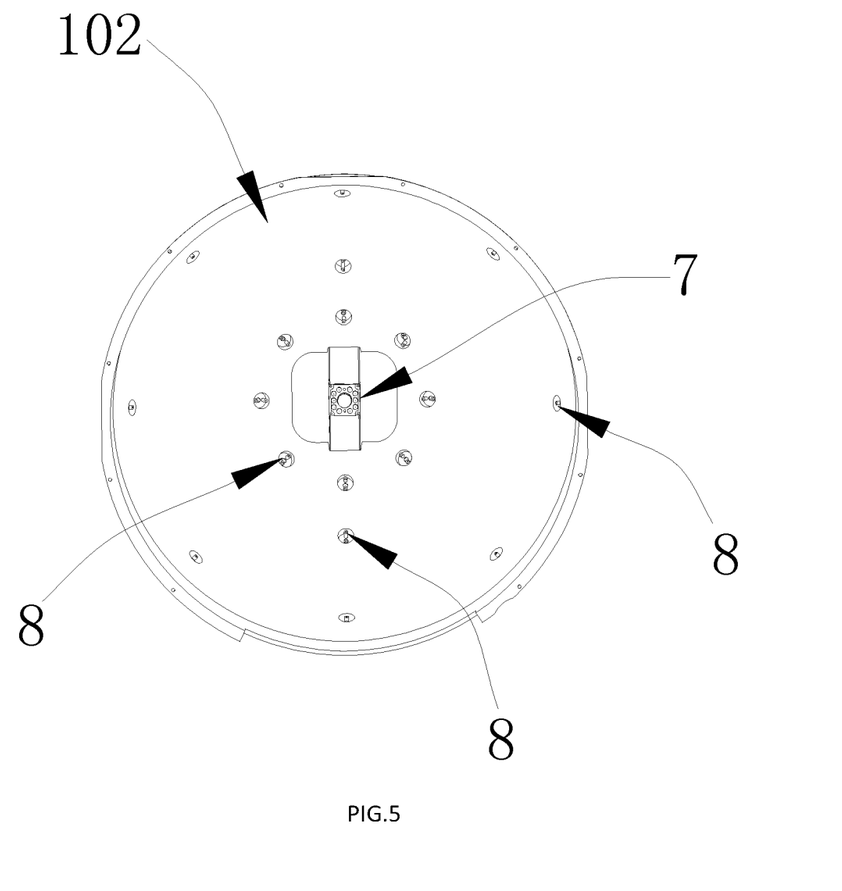
FIG. 5 is a front view of an inner housing in FIG. 4.

Further, as shown in FIG. 4 and FIG. 5, the data acquisition device includes at least one camera 7 and a plurality of guide lights 8, the camera and the plurality of guide lights are arranged in the inner housing respectively, where the camera, the eyepiece and the lens mechanism are located on a same axis, and the plurality of guide lights is distributed outwards circumferentially with the camera as a circle center.

Figure 6:
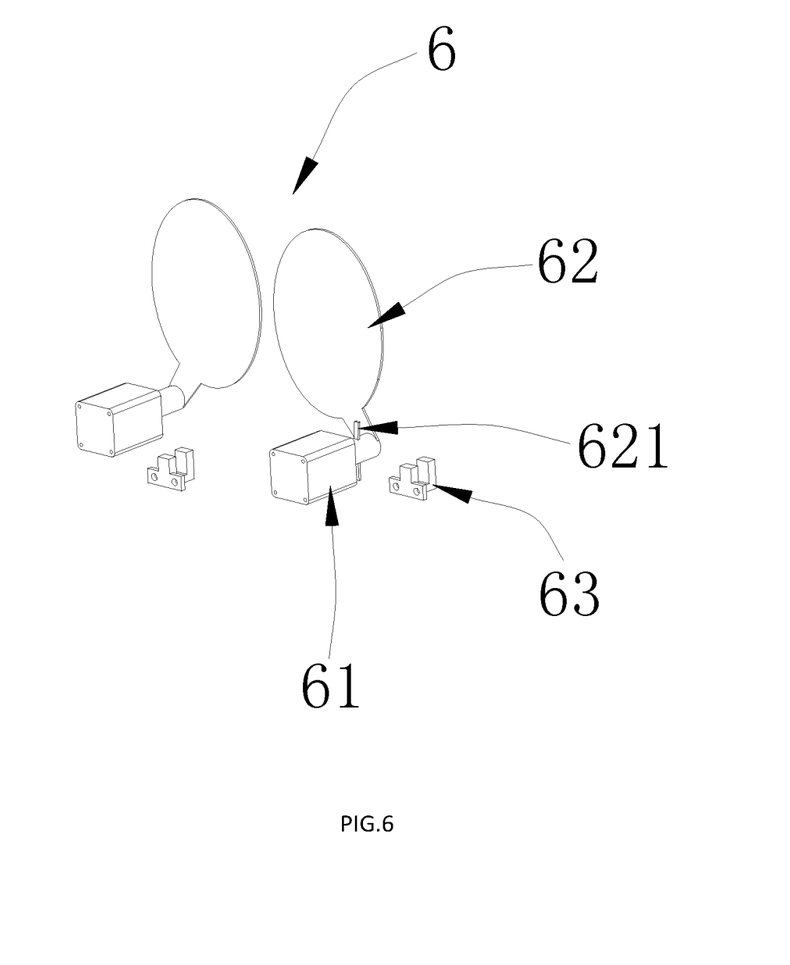
FIG. 6 is a schematic structure diagram of a covering device in FIG. 4.

Further, as shown in FIG. 6, the covering device 6 includes a rotating motor 61, a covering plate 62 and a limiting sensor 63, a rotating shaft of the rotating motor 61 is connected with the covering plate 62, the covering plate 62 is provided with a limiting strip 621, and when the covering plate 62 is in an uncovering or covering state, the limiting strip 621 is located in the limiting sensor 63.

As shown in FIG. 4, the control device includes a microprocessor and a display screen 104, the microprocessor is electrically connected with the lens mechanism, the covering device and the data acquisition device, respectively, and the display screen 104 is configured to display the test data.

It should be noted that in a preferred case, the lens mechanism is located between the front outer housing and the inner housing.

As a preferred technical solution, in the disclosure, a jaw lifting device may also be arranged, through which the head height of a user can be adjusted. The device is suitable for needs of different people.

As an inspection method of an inspection instrument of the disclosure:

An inspection method of a strabismus inspection instrument includes the following steps:

S1: observe through a window with both eyes, and look at a data acquisition device through a lens mechanism;

S2: cover, by a covering device, one eye that does not need to be inspected, and look at the data acquisition device with the other eye that is being inspected;

S3: start the lens mechanism and adjust an angle of refraction as needed;

S4: collect, by the data acquisition device, video data of the inspected eye; and S5: output the collected data.

It should be noted that the inspected eye looks at a flickering guide light of the data acquisition device during the inspection.

It should be further noted that the angle of refraction can be adjusted repeatedly and continuously.

Example

A user put the jaw on the jaw lifting device, a power supply was started, and an eye to be inspected was selected (if both eyes needed to be inspected, inspection was performed in order). At this time, the covering plate of the covering device rotated upward until the limiting strip was perpendicular to the limiting sensor so that the eye that did not need to be inspected (or waiting to be inspected) was covered.

Further, the inspected eye observed the lens mechanism through the window and looked at the data acquisition device. After the inspection was started, a plurality of guide lights on the data acquisition device would flicker in a certain mode, and the inspected eye of the user would continue to follow the guide lights flickering at different positions. At this time, the camera would capture video data.

Furthermore, the lens mechanism might be adjusted by 0 to 50 prism degrees under the action of the rotating mechanism. Specifically, when the rotating shaft of the motor of the rotating mechanism rotated, the worm was driven to rotate by the synchronous belt. Because the worm was connected with the worm gear in a meshing manner, the worm gear rotated synchronously, thereby further driving the lens mechanism connected to the rotating base. Furthermore, because the silicone sleeve was connected between the first lens group and the second lens group of the lens mechanism, when the rotating base drove the second lens group to rotate, the first lens group was not affected. Furthermore, because a closed space was formed between the first lens group, the second lens group and the silicone sleeve and the closed space was filled with silicone oil, when the second lens rotated (a vertical angle changes), light was refracted, and finally an angle of refraction was changed.

Finally, after the eye inspection was completed, the data acquisition device output data to a controller and the controller displayed the data on the display screen.

For those skilled in the art, various corresponding changes and modifications can be given according to the above technical solutions and concepts, and all these changes and modifications should be included in the protection scope of the claims of the disclosure.

What is claimed is:

1. An automatic strabismus detection mechanism for a strabismus inspection instrument having an outer housing composed of front and rear outer housings, and a window formed on the front outer housing, the automatic strabismus detection mechanism comprising:
   a housing coupled to the window of the front outer housing;
   an eyepiece arranged on the housing in positional correspondence with the window of the front outer housing; and
   a lens mechanism located on a same axis as the eyepiece is arranged in the housing, the lens mechanism having a rotating mechanism to adjust an angle of refraction.

2. The automatic strabismus detection mechanism according to claim 1, wherein the lens mechanism comprises a first lens group, a second lens group, a movable connecting member, and filling liquid, the first lens group and the second lens group are arranged at two ends of the movable connecting member respectively, an internal closed space is formed by the first lens group, the second lens group and the movable connecting member, the rotating mechanism is connected with the second lens group, when the rotating mechanism rotates, the second lens group rotates synchronously, and the filling liquid is filled in the closed space.

3. The automatic strabismus detection mechanism according to claim 2, wherein the first lens group is composed of a first sealing cover and a first lens installed therein, the second lens group is composed of a second sealing cover and a second lens installed therein, the movable connecting member is connected with the first sealing cover and the second sealing cover respectively in a sealing manner, and the rotating mechanism is connected with the second sealing cover.

4. The automatic strabismus detection mechanism according to claim 2, wherein the rotating mechanism comprises a motor, a worm, a worm gear, a rotating base, and a synchronous belt, two ends of the synchronous belt are arranged on a rotating shaft of the motor and one end of the worm respectively in a sleeving manner, the worm gear is connected with the worm in a meshing manner, the rotating base is arranged at the bottom of the worm gear, and the second lens group is connected with the rotating base.

5. A strabismus inspection instrument comprising:
   an outer housing composed of a front outer housing and a rear outer housing, an inner housing arranged in the outer housing, and a window formed on the front outer housing; and
   an automatic strabismus detection mechanism having a housing coupled to the window of the front outer housing; an eyepiece formed on the housing in positional correspondence with the window, and a lens mechanism located on a same axis as the eyepiece is arranged in the housing, the lens mechanism having a rotating mechanism to adjusts an angle of refraction; and further comprising:

a data acquisition device to collect and analyze obtained eyesight test data and output the eyesight test data;

a covering device, arranged on one side of a lens mechanism, to cover at least one eye to ensure that the other eye is inspected; and a control device to control the cooperative work of the lens mechanism, the covering device and the data acquisition device.

6. The strabismus inspection instrument according to claim 5, wherein the data acquisition device comprises at least one camera and a plurality of guide lights, the camera and the plurality of guide lights are arranged in the inner housing respectively, the camera, the eyepiece and the lens mechanism are located on a same axis, and the plurality of guide lights is distributed outwards circumferentially with the camera as a circle center.

7. The strabismus inspection instrument according to claim 5, wherein the covering device comprises a rotating motor, a covering plate and a limiting sensor, a rotating shaft of the rotating motor is connected with the covering plate, the covering plate is provided with a limiting strip, and when the covering plate is in an uncovering or covering state, the limiting strip is located in the limiting sensor.

8. The strabismus inspection instrument according to claim 5, wherein the control device comprises a microprocessor and a display screen, the microprocessor is electrically connected with the lens mechanism, the covering device and the data acquisition device, respectively, and the display screen displays the test data.

9. An inspection method of a strabismus inspection instrument having, an outer housing composed of a front outer housing and a rear outer housing, an inner housing arranged in the outer housing, and a window formed on the front outer housing; and an automatic strabismus detection mechanism having a housing coupled to the window of the front outer housing, an eyepiece formed on the housing in positional correspondence with the window; and a lens mechanism located on a same axis as the eyepiece is arranged in the housing, the lent mechanism having a rotating mechanism to adjusts an angle of refraction, and further comprising: a data acquisition device to collect and analyze obtained eyesight test data and output the eyesight test data, a covering device, arranged on one side of a lens mechanism, to cover at least one eye to ensure that the other eye is inspected; and a control device to control the cooperative work of the lens mechanism, the covering device and the data acquisition device, the inspection method, comprising:

observing through a window with both eyes, and looking at a data acquisition device through a lens mechanism;

covering, by a covering device, one eye that does not need to be inspected, and looking at the data acquisition device with the other eye that is being inspected;

starting the lens mechanism and adjusting an angle of refraction as needed;

collecting, by the data acquisition device, video data of the inspected eye; and outputting the collected data.

10. The inspection method of the strabismus inspection instrument according to claim 9, wherein the inspected eye looks at a flickering guide light of the data acquisition device during the inspection, and the angle of refraction can be adjusted repeatedly and continuously.

* * * * *